(12) United States Patent
Bharat et al.

(10) Patent No.: US 11,576,728 B2
(45) Date of Patent: Feb. 14, 2023

(54) INTERVENTIONAL TOOL STEPPER FOR ELECTROMAGNETIC TRACKING

(71) Applicant: KONINKLIJKE PHILIPS N.V., Eindhoven (NL)

(72) Inventors: Shyam Bharat, Arlington, MA (US); Ehsan Dehghan Marvast, New York, NY (US); Cynthia Ming-Fu Kung, New York, NY (US); Shriram Sethuraman, Briarcliff Manor, NY (US); Douglas Allen Stanton, Ossining, NY (US); Jochen Kruecker, Washington, DC (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 225 days.

(21) Appl. No.: 14/914,748

(22) PCT Filed: Sep. 18, 2014

(86) PCT No.: PCT/IB2014/064617
§ 371 (c)(1),
(2) Date: Feb. 26, 2016

(87) PCT Pub. No.: WO2015/040561
PCT Pub. Date: Mar. 26, 2015

(65) Prior Publication Data
US 2016/0206382 A1    Jul. 21, 2016

Related U.S. Application Data

(60) Provisional application No. 61/879,163, filed on Sep. 18, 2013.

(51) Int. Cl.
A61B 34/20    (2016.01)
A61B 17/34    (2006.01)
(Continued)

(52) U.S. Cl.
CPC .......... *A61B 34/20* (2016.02); *A61B 17/3403* (2013.01); *A61B 90/11* (2016.02);
(Continued)

(58) Field of Classification Search
CPC .. A61M 2025/0175; A61M 2025/0681; A61B 34/20; A61B 17/3403;
(Continued)

(56) References Cited

U.S. PATENT DOCUMENTS 5,555,251 A * 9/1996 Kinanen .............. G01R 33/383
324/318
2001/0041838 A1 11/2001 Holupka et al.
(Continued)

FOREIGN PATENT DOCUMENTS

DE    19905239 A1    8/2000

OTHER PUBLICATIONS

Muntener, M. et al., "Magnetic resonance imaging compatible robotic system for fully automated brachytherapy seed placement", Urology, 2006, 68(6): 1313-1317.

*Primary Examiner* — Brooke Labranche

(57) ABSTRACT

An interventional tool stepper (30) employing a frame (31), a carriage (33), an optional gear assembly (32), and an optional grid template(34). The frame (31) is structurally configured to be positioned relative to an anatomical region for holding an interventional tool (40) relative to the anatomical region. The carriage (33) is structurally configured to hold the interventional tool (40) relative to the anatomical region. The gear assembly (32) is structurally configured to translate and/or rotate the carriage (33) relative to the frame (31). The grid template (34) is structurally configured to guide one or more additional interventional tools (41) relative to the anatomical region. The frame (31), the carriage (33), the optional gear assembly (32) and the optional grid
(Continued)

template (34) have an electromagnetic-compatible material composition for minimizing any distortion by the interventional tool stepper (30) of an electromagnetic field.

15 Claims, 2 Drawing Sheets

(51) Int. Cl.
*A61B 90/11* (2016.01)
*A61B 90/00* (2016.01)

(52) U.S. Cl.
CPC .............. *A61B 2017/3409* (2013.01); *A61B 2017/3411* (2013.01); *A61B 2017/3413* (2013.01); *A61B 2034/2051* (2016.02); *A61B 2090/378* (2016.02)

(58) Field of Classification Search
CPC .... A61B 2034/2051; A61B 2017/3409; A61B 90/11; A61B 2017/34; A61B 2017/3413
See application file for complete search history.

(56) References Cited

U.S. PATENT DOCUMENTS

| | | |
|---|---|---|
| 2004/0059177 A1 | 3/2004 | Baltas et al. |
| 2004/0231683 A1* | 11/2004 | Eng .................. A61B 1/00158 128/899 |
| 2007/0255132 A1* | 11/2007 | Shalgi .................. G01V 3/104 600/424 |
| 2008/0108991 A1 | 5/2008 | Von Jako et al. |
| 2008/0216239 A1 | 9/2008 | Luginbuhl et al. |
| 2009/0259122 A1 | 10/2009 | Larson et al. |
| 2010/0041938 A1 | 2/2010 | Stoianovici et al. |
| 2011/0071380 A1* | 3/2011 | Goldenberg ........... A61B 5/055 600/411 |
| 2012/0265051 A1 | 10/2012 | Fischer et al. |
| 2013/0270997 A1* | 10/2013 | Zhao ...................... H05H 1/46 315/34 |
| 2014/0275987 A1* | 9/2014 | Bzostek ................ A61B 5/061 600/424 |
| 2015/0018685 A1 | 1/2015 | Barker et al. |
| 2015/0051861 A1 | 2/2015 | Krruecker et al. |

* cited by examiner

INTERVENTIONAL TOOL STEPPER FOR ELECTROMAGNETIC TRACKING

CROSS-REFERENCE TO PRIOR APPLICATIONS

This application is the U.S. National Phase application under 35 U.S.C. § 371 of International Application Serial No. PCT/IB2014/064617, filed on Sep. 18, 2014, which claims the benefit of U.S. Application Ser. No. 61/879,163, filed on Sep. 18, 2013. These applications are hereby incorporated by reference herein.

The present invention generally relates to an interventional tool stepper compatible with electromagnetic ("EM") tracking technology. The present invention specifically relates to an interventional tool stepper employing components having an EM-compatible material composition for minimizing any distortion by the interventional tool stepper of an electromagnetic field.

Generally, a stepper is utilized to hold/guide and if needed, translate/rotate interventional tool(s) for facilitating an interventional procedure (e.g., transperineal biopsy, internal radiation therapies such as permanent radioactive seed implants, temporary interstitial brachytherapy etc.)

More particularly, brachytherapy procedures involve the use of a stepper to hold and translate/rotate a transrectal ultrasound ("TRUS") probe within a patient. The stepper is also used to hold a grid/template in a fixed position with respect to the TRUS probe for guiding an insertion of needles/catheters into the patient.

For example, FIG. 1 illustrates a typical brachytherapy set-up involving a stepper 10 consisting of a frame 11, a gear assembly 12, a carriage 13 and a grid template 14. During the brachytherapy procedure, carriage 13 holds a TRUS probe 15 while gear assembly 12 is manually or automatically operated to translate and/or rotate TRUS probe 15 in and out of the patient's rectum. Once TRUS probe 15 is properly positioned within the patient's rectum, grid template 14 may be used to guide an insertion of a needle/catheter 16 into the patient to facilitate an implantation of radiation source(s) within the patient.

For this brachytherapy procedure, EM tracking technology may be utilized to track a positioning of TRUS probe 15 within the patient. EM tracking may also be utilized for navigation/guidance/mapping of needles, stylets and other interventional devices used in the procedure (e.g., needle/catheter 16). However, a major drawback with the use of EM tracking technology is that metallic equipment in the vicinity of the field of view ("FOV") of an EM field generator may cause distortions in the tracking of TRUS probe 15 and other EM-tracked devices. In particular, ferromagnetic metals as well as eddy currents generated by non-ferrous metals (e.g., aluminum) have the largest impact on spatial distortions of the EM field. Currently, the commercially available brachytherapy steppers contain significant amounts of metal. As a result, the EM tacking data is spatially distorted, which may result in inaccuracies in guidance, navigation and planning that may have a negative impact on treatment efficacy.

The present invention addresses this major drawback by providing an interventional tool stepper employing components having an EM-compatible material composition for minimizing any distortion by the interventional tool stepper of an electromagnetic field.

One form of the present invention is an interventional tool stepper employing a frame, a carriage, an optional gear assembly, and an optional grid template. The frame is structurally configured to be positioned relative to an anatomical region (e.g., a rectum of a patient) for holding an interventional tool (e.g., a TRUS probe) relative to the anatomical region. The carriage is structurally configured to hold the interventional tool relative to the anatomical region. The gear assembly is structurally configured to translate and/or rotate the carriage relative to the frame. The grid template is structurally configured to guide one or more additional interventional tools (e.g., needle(s), catheter(s), etc.) relative to the anatomical region. The frame, the carriage, the optional gear assembly and the optional grid template have an electromagnetic-compatible material composition (e.g., a biomedically-compliant plastic or a biomedically-compliant metal) for minimizing any distortion by the interventional tool stepper of an electromagnetic field.

A second form of the present invention is an interventional system employing the aforementioned interventional tool stepper and an electromagnetic field generator structurally configured to generate the electromagnetic field. The electromagnetic field generator may be attached or unattached to the interventional tool stepper.

The foregoing forms and other forms of the present invention as well as various features and advantages of the present invention will become further apparent from the following detailed description of various embodiments of the present invention read in conjunction with the accompanying drawings. The detailed description and drawings are merely illustrative of the present invention rather than limiting, the scope of the present invention being defined by the appended claims and equivalents thereof.

Figure 1:
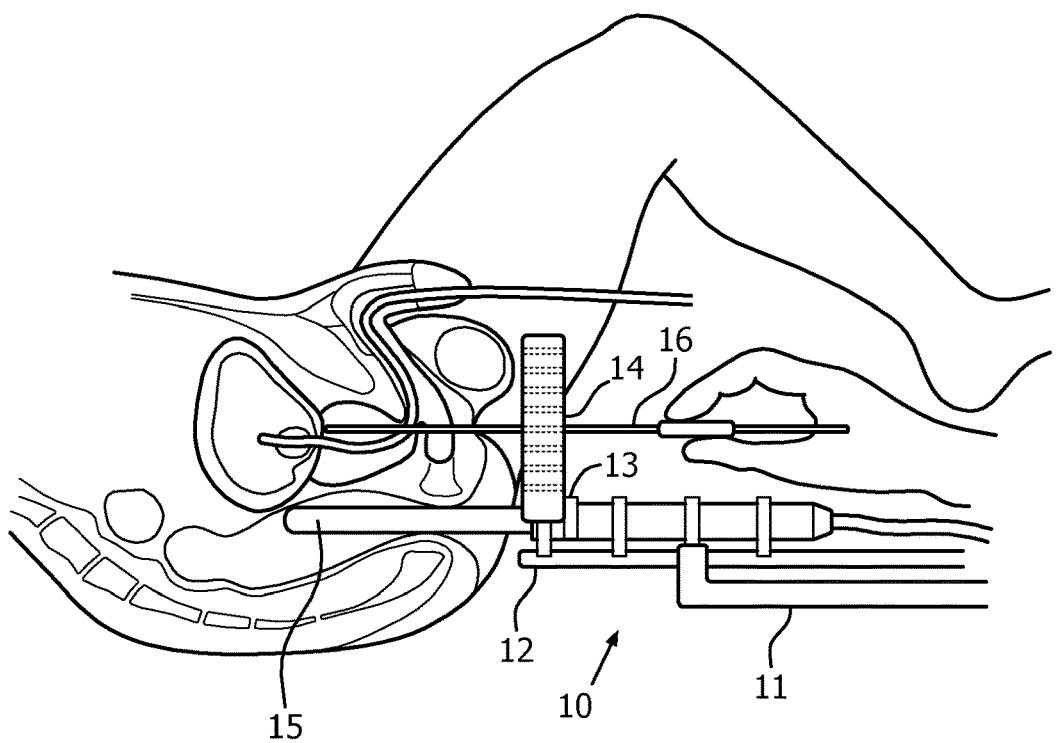
FIG. 1 illustrates an exemplary brachytherapy utilizing an ultrasound probe stepper as known in the art.
Figure 2:
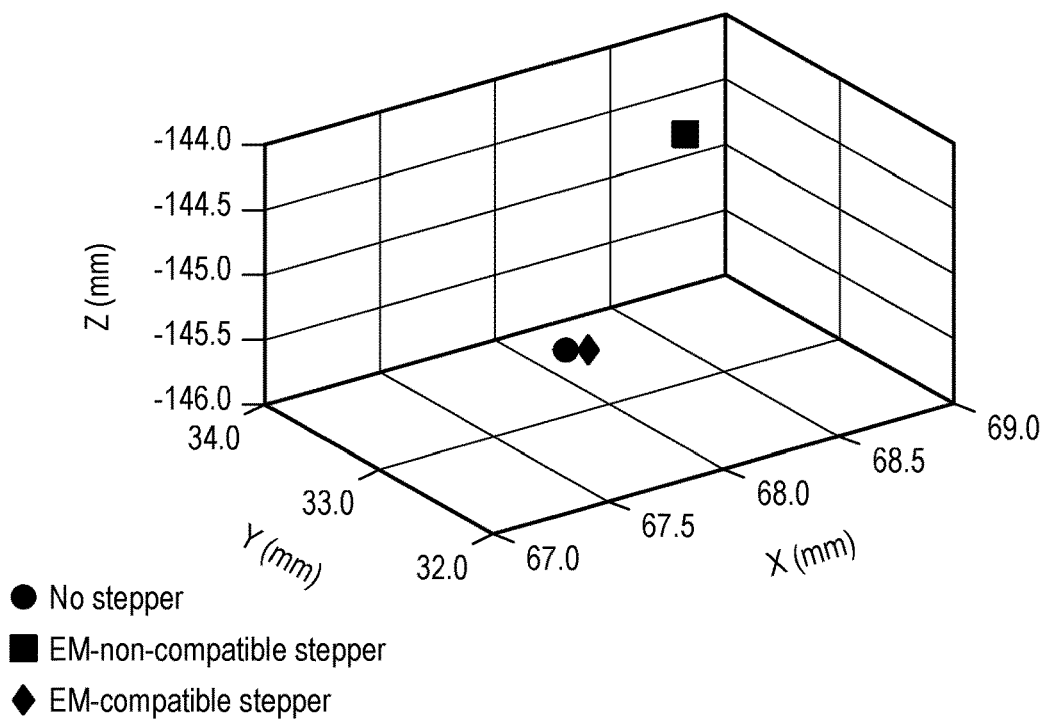
FIG. 2 illustrates comparative EM field distortion data of an EM-non-compatible stepper as known in the art and a EM-compatible stepper in accordance with the present invention.

The present invention is premised on an unpredictable discovery by the inventors of a comparative distortion of an EM field by an interventional tool steeper having a EM-non-compatible material composition as known in the art and a EM-compatible material composition of the present invention. To the point, FIG. 2 illustrates exemplary EM field distortion data for a EM-non-compatible stepper as known in the art, and a EM-compatible stepper of the present invention. Specifically, an EM-non-compatible stepper as known in the art has a material composition consisting of ferromagnetic metals or non-ferrous metals capable of generating eddy currents in the presence of the EM field (e.g., aluminum). By comparison, an EM-compatible stepper of the present invention has a material composition consisting of high-strength, non-EM-distorting biomedically compliant materials including, but not limited to, plastics and non-ferrous metals incapable of generating eddy currents in the presence of the EM field or capable of generating negligible eddy currents in the presence of the EM field.

As shown in FIG. 2, a XYZ data point • represents an average detected position of an EM sensor in an absence of an interventional tool stepper within the EM field. Of importance, even in an ideal clean environment, inherent noise is present in an EM tracking technology. For example, two (2) EM sensor position measurements taken in an ideal clean environment may be 0.1 mm apart due to the inherent noise. Consequently, the XYZ data point • represents an average detected position of an EM sensor in the context of the inherent noise of the EM tracking technology.

As related to the XYZ data point •, a XYZ data point ■ represents an average detected position of an EM sensor with an EM-non-compatible stepper within the EM field that has a 1.78 mm mean absolute deviation with the XYZ data point • yielding a consequential distortion of the EM field. By comparison, a XYZ data point ▲ represents an average detected position of an EM sensor with an EM-compatible stepper within the EM field that has a 0.06 mm mean absolute deviation with the XYZ data point • yielding a negligible distortion of the EM field.

The comparative distortion data teaches the EM-compatible stepper practically imposes negligible distortion of the EM field relative to the inherent noise of the EM tracking technology. Thus, the material composition of the components of the EM-compatible stepper may be considered to minimize distortion of the EM field equivalent to the inherent noise of the EM tracking technology.

Figure 3:
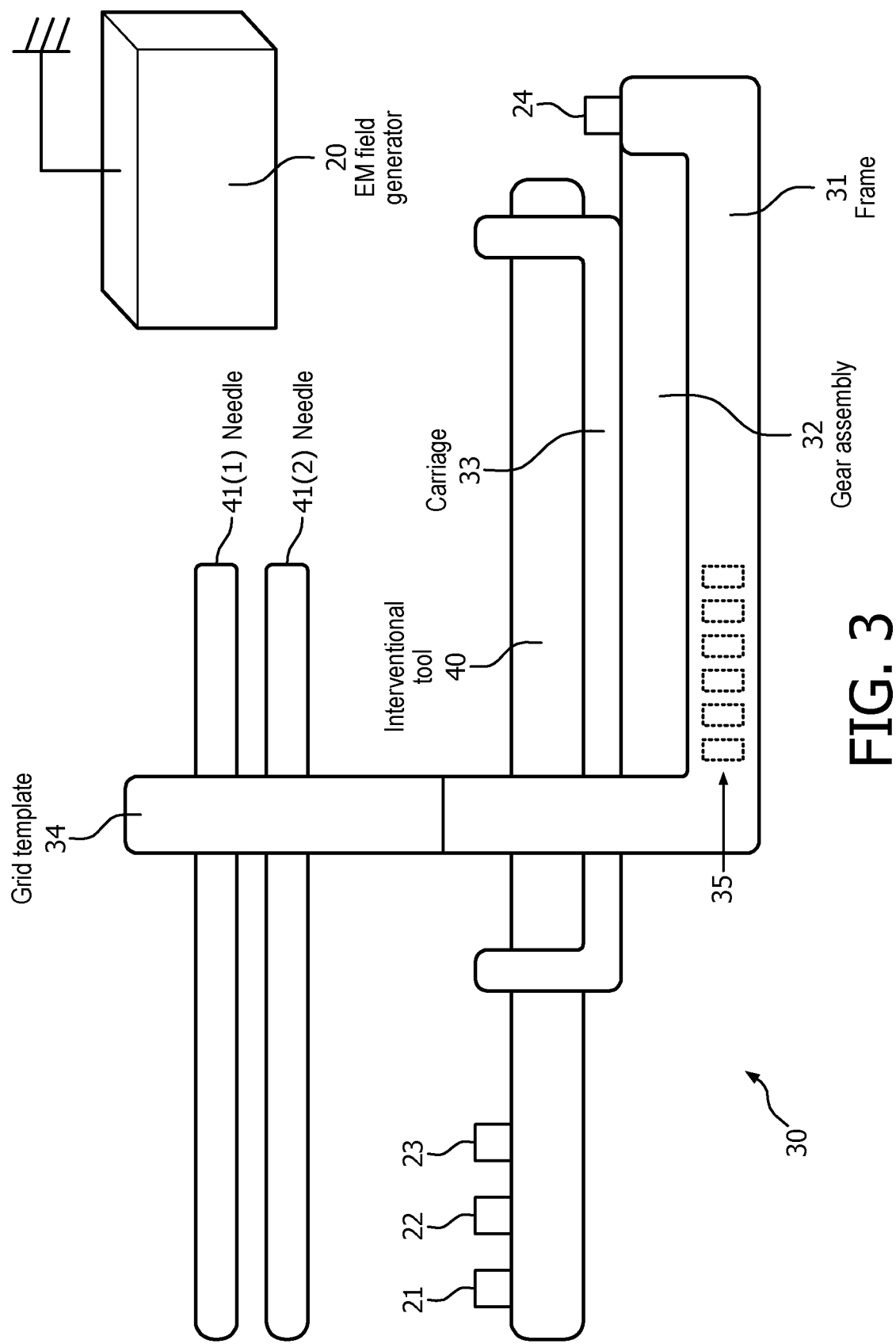
FIG. 3 illustrates an exemplary embodiment of a EM-compatible stepper in accordance with the present invention.

To facilitate a further understanding of an EM-compatible stepper of the present invention, FIG. 3 illustrates an EM-compatible stepper 30 employing a frame 31, an optional gear assembly 32, a carriage 33, and an optional grid template 34 as known in the art. Frame 31 is structurally configured to be positioned relative to an anatomical region (not shown) (e.g., a rectum of a patient) for an insertion of an interventional tool 40 (e.g., a TRUS probe) within the anatomical region. Carriage 33 is structurally configured to support the insertion of the interventional tool 40 into the anatomical region. Gear assembly 32 is structurally configured to translate and/or rotate, manually or motor-driven, carriage 33 relative to frame 31.

In operation, an EM field generator 20 generates an EM field (not shown) for tracking interventional tool 40 via EM sensors 21-23 as known in the art. The EM field may also track the needles 41 and other interventional equipment. Frame 31, gear assembly 32 and carriage 33 have an EM-compatible material composition for minimizing any distortion by interventional tool stepper 30 of the EM field.

In one embodiment, the EM-compatible material composition consists of USP Class VI plastic(s) including, but not limited to, polyetheretherketone ("PEEK"), polyaryletherrsulfone ("Radel") and EPO-TEK (a curable epoxy adhesive and encapsulant).

In another embodiment, the EM-compatible material composition consists of non-ferrous metals incapable of generating eddy currents in the presence of the EM field or capable of generating negligible eddy current in the presence of the EM field including, but not limited, to titanium and medical-grade stainless steel (300 series).

In yet another embodiment, frame 31, optional gear assembly 32, carriage 33, and optional grid template 34 are designed without large surfaces whereby the EM-compatible material composition may consist of non-ferrous metals capable of generating eddy currents in the presence of the EM field (e.g., aluminum). For example, as shown in FIG. 3, slots 35 may be designed in frame 31 to avoid continuity in the surface of frame 31.

In practice, while all components of an EM-compatible stepper of the present invention must have an EM-compatible material composition, the material composition may or may not vary between components. For example, a frame, a carriage and a grid template may be manufactured from a plastic (e.g., UPS Class IV), and the gear assembly may be manufactured from a metal (e.g., titanium).

Also in practice, an EM-compatible stepper of the present invention may have any currently known or unknown structural configuration suitable for holding/guiding and/or translating/rotation an interventional tool (e.g., a TRUS probe). For example, the Classic Stepper provided by CIVCO Medical Solutions is a candidate for a material composition consisting of high-strength, non-EM-distorting biomedically complaint materials of the present invention.

Furthermore in practice, one or more EM sensors may be attached to one or more components of an EM-compatible stepper of the present invention for purposes of facilitating an image reconstruction generated by the interventional tool and/or as a reference for other EM tools. Also, the EM field generator may be attached to the EM-compatible stepper with the EM sensor(s) being spatially located at a reference.

Referring to FIGS. 2 and 3, the material composition of the EM-compatible stepper is equivalent to the inherent noise of EM tracking technology in terms of a distortion of the EM field. Those having ordinary skill in the art will appreciate numerous benefits of the present invention including, but not limited to, a utilization of an EM-compatible steeper for any interventional therapy system employing EM tracking technology that requires stable position of the interventional tool (e.g., TRUS probe) and translational/rotational adjustments in one of more directions.

While various embodiments of the present invention have been illustrated and described, it will be understood by those skilled in the art that the embodiments of the present invention as described herein are illustrative, and various changes and modifications may be made and equivalents may be substituted for elements thereof without departing from the true scope of the present invention. In addition, many modifications may be made to adapt the teachings of the present invention without departing from its central scope. Therefore, it is intended that the present invention not be limited to the particular embodiments disclosed as the best mode contemplated for carrying out the present invention, but that the present invention includes all embodiments falling within the scope of the appended claims.

The invention claimed is:
1. An interventional tool stepper, comprising:
a frame structurally configured to be positioned relative to an anatomical region for holding an interventional tool relative to the anatomical region;
a carriage coupled to the frame, the carriage structurally configured to hold the interventional tool relative to the anatomical region; and
a grid template coupled to at least one of the frame and the carriage, the grid template structurally configured to hold at least one additional interventional tool relative to the anatomical region and guide insertion of the at least one additional interventional tool into the anatomical region,
wherein the frame, the carriage, and the grid template have an electromagnetic-compatible material composition for minimizing any distortion by the interventional tool stepper of an electromagnetic field at least partially encircling the interventional tool stepper, and
wherein (i) the electromagnetic-compatible material composition of the grid template includes at least one nonferrous metal capable of generating eddy current in the presence of the electromagnetic field and (ii) the grid template is configured with at least one slot in a surface thereof for minimizing any induction of eddy currents generated in the grid template.
2. The interventional tool stepper of claim 1, wherein the electromagnetic-compatible material composition includes at least one of a biomedically-compliant plastic and a biomedically-compliant nonferrous metal.

3. The interventional tool stepper of claim 1, wherein the electromagnetic-compatible material composition is configured for minimizing any distortion by the interventional tool stepper of the electromagnetic field comparable to an inherent noise associated with the electromagnetic field.

4. The interventional tool stepper of claim 1, further comprising:
at least one electromagnetic sensor positioned relative to the frame and the carriage for electromagnetically tracking the interventional tool stepper.

5. The interventional tool stepper of claim 1, further comprising:
a gear assembly coupling the carriage to the frame, the gear assembly being structurally configured to at least one of translate and rotate the carriage relative to the frame, wherein the gear assembly has the electromagnetic-compatible material composition for minimizing any distortion by the interventional tool stepper of an electromagnetic field at least partially encircling the interventional tool stepper and the gear assembly includes at least one slot in a surface thereof for minimizing any induction of eddy currents by the interventional tool stepper.

6. The interventional tool stepper of claim 1, wherein the frame comprises a material that generates eddy currents in a presence of an electromagnetic field.

7. The interventional tool stepper of claim 1, wherein at least one of the frame and the carriage includes at least one slot in a surface thereof for minimizing any induction of eddy currents by the interventional tool stepper.

8. An interventional system, comprising:
an electromagnetic field generator structurally configured to generate an electromagnetic field; and
an interventional tool stepper including:
a frame structurally configured to be positioned relative to an anatomical region for holding an interventional tool relative to the anatomical region,
a carriage coupled to the frame, the carriage being structurally configured to hold the interventional tool relative to the anatomical region, and
a grid template coupled to at least one of the frame and the carriage, the grid template structurally configured to hold at least one additional interventional tool relative to the anatomical region and guide insertion of the at least one additional interventional tool into the anatomical region,
wherein the frame, the carriage, and the grid template have an electromagnetic-compatible material composition for minimizing any distortion by the interventional tool stepper of the electromagnetic field at least partially encircling the interventional tool stepper, and
wherein the grid template including (i) the electromagnetic-compatible material composition of the grid template includes at least one nonferrous metal capable of generating eddy current in the presence of the electromagnetic field and (ii) the grid template is configured with at least one slot in a surface thereof for minimizing any induction of eddy currents generated in the grid template.

9. The interventional system of claim 8, wherein the electromagnetic-compatible material composition includes at least one of a biomedically-compliant plastic and a biomedically-compliant nonferrous metal.

10. The interventional system of claim 8, wherein the electromagnetic-compatible material composition is configured for minimizing any distortion by the interventional tool stepper of the electromagnetic field comparable to an inherent noise associated with the electromagnetic field.

11. The interventional system of claim 8, further comprising:
at least one electromagnetic sensor positioned relative to the frame and the carriage for electromagnetically tracking the interventional tool stepper.

12. The interventional system of claim 8, further comprising:
a gear assembly coupling the carriage to the frame, the gear assembly being structurally configured to at least one of translate and rotate the carriage relative to the frame,
wherein the gear assembly has the electromagnetic-compatible material composition for minimizing any distortion by the interventional tool stepper of an electromagnetic field at least partially encircling the interventional tool stepper and the gear assembly includes at least one slot in a surface thereof for minimizing any induction of eddy currents by the interventional tool stepper.

13. The interventional system of claim 8, wherein the electromagnetic field generator is unattached to the interventional tool stepper.

14. The interventional system of claim 8, wherein the frame comprises a material that generates eddy currents in a presence of the electromagnetic field.

15. The interventional system of claim 8, wherein at least one of the frame and the carriage includes at least one slot in a surface thereof for minimizing any induction of eddy currents by the interventional tool stepper.

* * * * *